(12) United States Patent
Ressel

(10) Patent No.: US 11,478,319 B1
(45) Date of Patent: Oct. 25, 2022

(54) GLOVE DISPENSER SUPPORTED ON A RACK

(71) Applicant: Dorothy Ressel Intellectual Properties, Inc., Apache Junction, AZ (US)

(72) Inventor: Dorota Ressel, Apache Junction, AZ (US)

( * ) Notice: Subject to any disclaimer, the term of this patent is extended or adjusted under 35 U.S.C. 154(b) by 36 days.

(21) Appl. No.: 17/191,269

(22) Filed: Mar. 3, 2021

Related U.S. Application Data

(63) Continuation-in-part of application No. 15/887,962, filed on Feb. 2, 2018, now Pat. No. 10,945,802.

(60) Provisional application No. 62/600,148, filed on Feb. 13, 2017.

(51) Int. Cl.
| | |
|---|---|
| *A61B 42/40* | (2016.01) |
| *B65D 65/42* | (2006.01) |
| *B65D 75/12* | (2006.01) |
| *B65D 1/08* | (2006.01) |
| *B65D 1/28* | (2006.01) |
| *B65D 83/08* | (2006.01) |
| *B65D 81/28* | (2006.01) |

(52) U.S. Cl.
CPC .............. *A61B 42/40* (2016.02); *B65D 65/42* (2013.01); *B65D 75/12* (2013.01); *B65D 81/28* (2013.01); *B65D 83/0805* (2013.01)

(58) Field of Classification Search
CPC ......... A61B 42/40; A61B 50/22; A61B 42/22; A61B 42/10; A61B 42/50; A61B 50/20; B65D 83/0805; B65D 83/0894; B65D 83/0835; B65D 85/18; A41D 19/0055; A41D 9/015

USPC .................................................. 221/207, 307
See application file for complete search history.

(56) References Cited

U.S. PATENT DOCUMENTS

| | | | |
|---|---|---|---|
| 361,852 A * | 4/1887 | Alderman | A47F 1/128 211/54.1 |
| 1,039,635 A | 9/1912 | Beers | |
| 2,023,542 A | 12/1935 | Peck | |
| 2,519,839 A * | 8/1950 | Leisen | B65D 19/0026 108/57.32 |
| 3,064,652 A * | 11/1962 | Corcoran | A61J 1/10 215/253 |

(Continued)

FOREIGN PATENT DOCUMENTS

| | | | | |
|---|---|---|---|---|
| EP | 0305236 A1 * | 3/1989 | ............. | B65D 83/08 |
| EP | 1321372 A1 * | 6/2003 | ............. | A47F 9/042 |

(Continued)

*Primary Examiner* — Rakesh Kumar

(74) *Attorney, Agent, or Firm* — Adam R. Stephenson, Ltd.

(57) ABSTRACT

Implementations of glove dispensers may include a sealed first end and a sealed second end opposite the sealed first end, a first plurality of openings extending through the first sealed end, a second plurality of openings extending through the second sealed end, and a first opening extending through a sidewall of the flexible bag. Implementations of glove dispensers may also include a first plurality of gloves included within the flexible bag. A cuff of a glove of the first plurality of gloves may be exposed through the first opening. The first plurality openings and the second plurality of openings may be configured to couple to a dispenser rack. The glove dispenser may be configured to stretch between the sealed first end and the sealed second end when coupled to the dispenser rack.

18 Claims, 8 Drawing Sheets

(56) References Cited

U.S. PATENT DOCUMENTS

| | | | |
|---|---|---|---|
| 3,255,951 A | 6/1966 | Chan | |
| 3,281,056 A | 10/1966 | Kugler | |
| 3,306,492 A | 2/1967 | Kugler | |
| 3,312,339 A | 4/1967 | Million | |
| 3,317,037 A | 5/1967 | Russell | |
| 3,646,723 A | 3/1972 | Meroney | |
| 4,150,807 A * | 4/1979 | Manso | A47B 23/06 |
| | | | 248/452 |
| 4,207,983 A | 6/1980 | Wolske | |
| 4,216,863 A | 8/1980 | Seymour-Smith | |
| 4,470,571 A | 9/1984 | Hartman | |
| 4,537,330 A | 8/1985 | Gelbard | |
| 4,550,856 A | 11/1985 | Ballmann | |
| 4,611,719 A * | 9/1986 | Dudek | B41J 11/58 |
| | | | D18/49 |
| RE32,443 E * | 6/1987 | Kalal | B65D 75/54 |
| | | | 206/466 |
| 4,759,639 A * | 7/1988 | DeMatteis | B65D 33/001 |
| | | | 383/7 |
| 4,779,996 A | 10/1988 | Sengewald | |
| 4,844,293 A | 7/1989 | McLaughlin | |
| 4,988,213 A * | 1/1991 | Mattle | B65D 33/001 |
| | | | 493/926 |
| 5,044,494 A | 9/1991 | Tamura | |
| 5,100,000 A | 3/1992 | Huseman | |
| 5,131,564 A | 7/1992 | Plonkey | |
| 5,338,117 A * | 8/1994 | Kucksdorf | B65D 75/58 |
| | | | 383/906 |
| 5,386,910 A | 2/1995 | Liss | |
| 5,457,944 A * | 10/1995 | Lipes | B65D 33/14 |
| | | | 53/390 |
| 5,524,763 A * | 6/1996 | Wile | B65B 43/14 |
| | | | 221/63 |
| 5,562,213 A | 10/1996 | Wile | |
| 5,655,682 A * | 8/1997 | Hoffrichter | B65D 83/0805 |
| | | | 221/45 |
| 5,816,440 A | 10/1998 | Shields et al. | |
| 5,860,529 A | 1/1999 | Smithson | |
| 5,862,944 A * | 1/1999 | Scherr | B65D 33/14 |
| | | | 221/63 |
| 5,927,660 A | 7/1999 | McNerney | |
| 5,941,392 A | 8/1999 | Huang | |
| 5,954,432 A | 9/1999 | Laudenberg | |
| 6,042,063 A | 3/2000 | Kerr | |
| 6,179,126 B1 | 1/2001 | Smithson | |
| 6,264,035 B1 | 7/2001 | Petrie | |
| 6,286,681 B1 | 9/2001 | Wilfong | |
| 6,325,243 B1 | 12/2001 | Bennett | |
| 6,382,429 B1 | 5/2002 | Yeh | |
| 6,416,220 B1 | 7/2002 | Fox | |
| 6,578,729 B2 | 6/2003 | Grinberg | |
| 6,708,841 B2 | 3/2004 | Baughman | |
| 7,063,233 B2 | 6/2006 | Jordan et al. | |
| 7,150,374 B1 | 12/2006 | Camps | |
| 7,163,339 B1 | 1/2007 | Hefner | |
| 7,600,641 B2 | 10/2009 | Burgess | |
| 7,699,189 B2 | 4/2010 | Tramontina | |
| 3,016,111 A1 | 9/2011 | Wilson | |
| 3,067,072 A1 | 11/2011 | Tan | |
| 8,104,959 B2 * | 1/2012 | Lucas | B65D 75/566 |
| | | | 383/88 |
| 8,550,717 B2 | 10/2013 | Hefner | |
| 8,567,618 B2 | 10/2013 | Tan | |
| 8,784,967 B2 * | 7/2014 | Frei | B65B 25/048 |
| | | | 428/113 |
| 8,857,134 B2 | 10/2014 | Lucas | |
| 8,985,338 B2 | 3/2015 | Fux | |
| 9,630,375 B2 | 4/2017 | Frei | |
| 9,770,123 B2 | 9/2017 | Tan | |
| 10,144,575 B2 | 12/2018 | Tan | |
| 10,207,858 B2 | 2/2019 | Tan | |
| 10,414,577 B2 * | 9/2019 | Modha | B65D 83/0817 |
| 10,479,541 B2 | 11/2019 | DeMatteis | |
| 2001/0023873 A1 | 9/2001 | Wile | |
| 2002/0084279 A1 * | 7/2002 | Lickstein | A47K 10/42 |
| | | | 221/24 |
| 2002/0139811 A1 * | 10/2002 | Tramontina | A47K 10/424 |
| | | | 221/197 |
| 2003/0111381 A1 * | 6/2003 | Borrisuttanakul | A47F 9/042 |
| | | | 206/554 |
| 2003/0116580 A1 * | 6/2003 | Baughman | A61B 42/40 |
| | | | 221/45 |
| 2004/0035896 A1 | 2/2004 | LaPace | |
| 2005/0103679 A1 | 5/2005 | Smithson | |
| 2005/0105832 A1 | 5/2005 | Trinko | |
| 2005/0147331 A1 | 7/2005 | Sway | |
| 2006/0065680 A1 * | 3/2006 | LaPace | D06F 89/02 |
| | | | 223/37 |
| 2006/0072856 A1 | 4/2006 | Su | |
| 2006/0102809 A1 | 5/2006 | Broeders | |
| 2006/0215941 A1 | 9/2006 | Golbert | |
| 2007/0215628 A1 * | 9/2007 | Tramontina | A61B 42/40 |
| | | | 221/35 |
| 2007/0215630 A1 | 9/2007 | Tramontina | |
| 2007/0261975 A1 * | 11/2007 | Rabinoff | A45C 13/03 |
| | | | 206/287.1 |
| 2008/0230560 A1 * | 9/2008 | Powers | A45D 34/00 |
| | | | 264/250 |
| 2008/0277308 A1 | 11/2008 | Simhaee | |
| 2009/0268990 A1 | 10/2009 | Wilson | |
| 2011/0293203 A1 | 12/2011 | Wilson | |
| 2012/0160732 A1 | 6/2012 | Tan | |
| 2012/0298689 A1 | 11/2012 | Cohen | |
| 2013/0200093 A1 * | 8/2013 | Carlson | B65D 83/0811 |
| | | | 221/46 |
| 2013/0248554 A1 * | 9/2013 | Robin | B65D 85/671 |
| | | | 221/185 |
| 2014/0061220 A1 * | 3/2014 | Kowal | B65D 83/0805 |
| | | | 221/135 |
| 2015/0072849 A1 | 3/2015 | Tan | |
| 2015/0081003 A1 | 3/2015 | Wainwright | |
| 2015/0108158 A1 | 4/2015 | Fan | |
| 2015/0266655 A1 * | 9/2015 | Duffy | A41D 13/11 |
| | | | 29/428 |
| 2016/0143490 A1 | 5/2016 | Yamada | |
| 2016/0185508 A1 | 6/2016 | Fan | |
| 2016/0302626 A1 * | 10/2016 | D'Hiet | A47K 10/421 |
| 2016/0304276 A1 | 10/2016 | Castro | |
| 2017/0055727 A1 | 3/2017 | Tan | |
| 2018/0037356 A1 | 2/2018 | DeMatteis | |
| 2018/0099469 A9 | 4/2018 | Tan | |
| 2018/0111744 A1 * | 4/2018 | Modha | B65D 85/18 |
| 2018/0140026 A1 | 5/2018 | Nijmeh | |
| 2018/0162628 A1 * | 6/2018 | Modha | A61B 42/40 |
| 2018/0186552 A1 | 7/2018 | DeMatties | |
| 2018/0318154 A1 | 11/2018 | Louwrens | |
| 2018/0362236 A1 * | 12/2018 | Dieringer | B65D 83/0805 |
| 2019/0071239 A1 | 3/2019 | Tan | |
| 2019/0135527 A1 | 5/2019 | Tan | |
| 2019/0231096 A1 | 8/2019 | Bacallao | |
| 2019/0239974 A1 | 8/2019 | Ressel | |
| 2020/0094485 A1 | 3/2020 | Rabiea | |

FOREIGN PATENT DOCUMENTS

| | | | | |
|---|---|---|---|---|
| EP | 3012212 A1 * | 4/2016 | | A47K 10/20 |
| GB | 2495023 A * | 3/2013 | | A61B 42/40 |
| GB | 2495023 A | 3/2013 | | |
| GB | 2510428 A | 8/2014 | | |
| GB | 2519839 A * | 5/2015 | | A61B 42/40 |
| GB | 2519839 B | 9/2015 | | |
| GB | 2528242 A * | 1/2016 | | A61B 42/40 |
| GB | 2528242 A | 1/2016 | | |
| WO | WO-2007001611 A1 * | 1/2007 | | A47K 10/424 |
| WO | WO-2020003074 A1 * | 1/2020 | | A61B 42/40 |

* cited by examiner

GLOVE DISPENSER SUPPORTED ON A RACK

CROSS REFERENCE TO RELATED APPLICATIONS

This document claims the benefit of the filing date of U.S. Provisional Patent Application 62/600,148, entitled "Packing System for Medical Disposable Gloves with the Method for External Extraction Reducing Contamination" to Dorota Ressel which was filed on Feb. 13, 2017, the disclosure of which is hereby incorporated entirely herein by reference.

This application is a continuation-in-part application of the earlier U.S. Utility Patent Application to Dorota Ressel entitled "Packing System for Medical Disposable Gloves with the Method for External Extraction Reducing Contamination," application Ser. No. 15/887,962, filed Feb. 2, 2018, the disclosure of which is hereby incorporated entirely herein by reference.

BACKGROUND

1. Technical Field

This disclosure relates to a method of packing and dispensing disposable gloves and includes the new container and the system for carrying out this method.

2. Background

Disposable gloves are used in many fields and it is in medicine and diagnostics that the necessity of preserving them in an aseptic state is particularly essential. Studies carried out at American hospitals and clinics show that on average at least 50% of disposable gloves used by personnel are contaminated and in the case of gloves extracted from boxes placed close to water sources this share reaches 75%. Use of gloves often gives a false sense of safety which also results in the personnel not recognizing the necessity of careful disinfection of the hands or the necessity of careful drying of the hands before inserting hands into the boxes that contain the gloves.

From the description of U.S. Pat. No. 6,708,841 B2 there is known a wall-mountable glove dispenser into which a box of gloves is placed which enables dispensing of gloves.

From the description of U.S. Pat. No. 7,063,233B2 there is known a glove dispenser which enables one-off dispensing of a selected number of gloves.

From the description of U.S. Pat. No. 5,044,494A there is known a packaging case for packing either left-hand or right: hand gloves.

From the description of U.S. Pat. No. 7,699,189B2 there is known a glove dispenser in which gloves are tilted towards the opening through which they are dispensed to facilitate the extracting of each glove. The dispenser is configured in such a manner that a portion of the glove protrudes from the opening making it easier to grip and pull out.

From the description of U.S. Pat. No. 4,844,293A there is known a box for thin disposable gloves where the design of the box makes it possible to pull out single gloves.

From the description of U.S. Pat. No. 5,655,682 there is known a system of dispensing products consisting of a package of disposable plastic sheets that can be removed from the package one at a time to unpack the articles, e.g. gloves.

From the description of U.S. Pat. No. 5,816,440 there is known a system of dispensing disposable gloves where it is only the cuff of a single glove that protrudes from the dispensing hole and extracting one glove results in pulling the cuff of the next glove outside.

From the description of Patent GB2495023 there is known a glove dispenser where gloves are pushed upwards to facilitate taking them out of the pack. Gloves are arranged in such a manner that they can be taken out by touching only the cuff.

None of the solutions described above protect the packed gloves in a sufficient manner nor is it easy to implement packaging in mass production.

SUMMARY

Implementations of glove dispensers may include a sealed first end and a sealed second end opposite the sealed first end, a first plurality of openings extending through the first sealed end, a second plurality of openings extending through the second sealed end, and a first opening extending through a sidewall of the flexible bag. Implementations of glove dispensers may also include a first plurality of gloves included within the flexible bag. A cuff of a glove of the first plurality of gloves may be exposed through the first opening. The first plurality openings and the second plurality of openings may be configured to couple to a dispenser rack. The glove dispenser may be configured to stretch between the sealed first end and the sealed second end when coupled to the dispenser rack.

Implementations of glove dispensers may include one, all, or any of the following:

Implementations of the glove dispenser may include a perforated slit formed in the sidewall of the flexible bag and extending from the opening.

An interior of the flexible bag may be coated with a biocide.

Implementations of glove dispensers may include a second opening extending through the sidewall of the flexible bag.

Implementations of glove dispensers may include a second plurality of gloves included within the flexible bag. A cuff of a glove of the second plurality of gloves may be accessible through the second opening.

Implementations of glove dispensing systems may include a flexible bag including a sealed first end and a sealed second end. The sealed first end may be opposite the sealed second end. Implementations of the flexible bag may include an opening extending through a sidewall of the flexible bag. Implementations of glove dispensing systems may include a plurality of gloves included within the flexible bag. A cuff of a glove of the plurality of gloves may be accessible through the opening. Implementations of glove dispensing systems may also include a dispenser rack coupled to the flexible bag. The dispenser rack may be configured to apply tension to the flexible bag between the sealed first end and the sealed second end.

Implementations of glove dispensing systems may include one, all, or any of the following:

The dispenser rack may include a plurality of springs configured to stretch the flexible bag between the sealed first end and the sealed second end.

The plurality of springs may be coupled to the sealed first end.

The plurality of springs may be coupled to the sealed second end.

The dispenser rack may stretch the flexible bag and compress the plurality of gloves between two inner sidewalls of the flexible bag forming a seal between a first inner sidewall of the two inner sidewalls of flexible bag and the glove accessible through the opening.

The opening may be closable.

Implementations of glove dispensing systems may include a flexible bag including a sealed first end and a sealed second end, a first opening extending through a sidewall the flexible bag, and a second opening extending through the sidewall of the flexible bag. Implementations of glove dispensing systems may also include a first plurality of gloves included within the flexible bag. A cuff of a glove of the first plurality of gloves may be accessible through the first opening. Implementations of glove dispensing systems may also include a second plurality of gloves included within the flexible bag and a dispenser rack coupled to the flexible bag. A cuff of a glove of the second plurality gloves may be accessible through the second opening. The dispenser rack may be configured to apply tension to the flexible bag between the sealed first end and the sealed second end.

Implementations of glove dispensing systems may include one, all, or any of the following:

The dispenser rack may include a plurality of springs configured to stretch the flexible bag between the sealed first end and the sealed second end.

The plurality of springs may be coupled to a plurality of openings included in the sealed first end.

The dispenser rack may stretch the flexible bag and compress the first plurality of gloves between two inner sidewalls of the flexible bag, thereby forming a first seal between a first inner sidewall of the two inner sidewalls of the flexible bag and the glove accessible through the first opening.

The dispenser rack may stretch the flexible bag and compress the second plurality of gloves between two inner sidewalls of the flexible bag, thereby forming a second seal between the first inner sidewall of the two inner sidewalls of the flexible bag and the glove accessible through the second opening.

The first opening may be closable and the second opening may be closable.

The first plurality of gloves may include right-handed gloves and the second plurality of gloves may include left-handed gloves.

An interior of the flexible bag may be coated with a biocide.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DESCRIPTION

Figure 1:
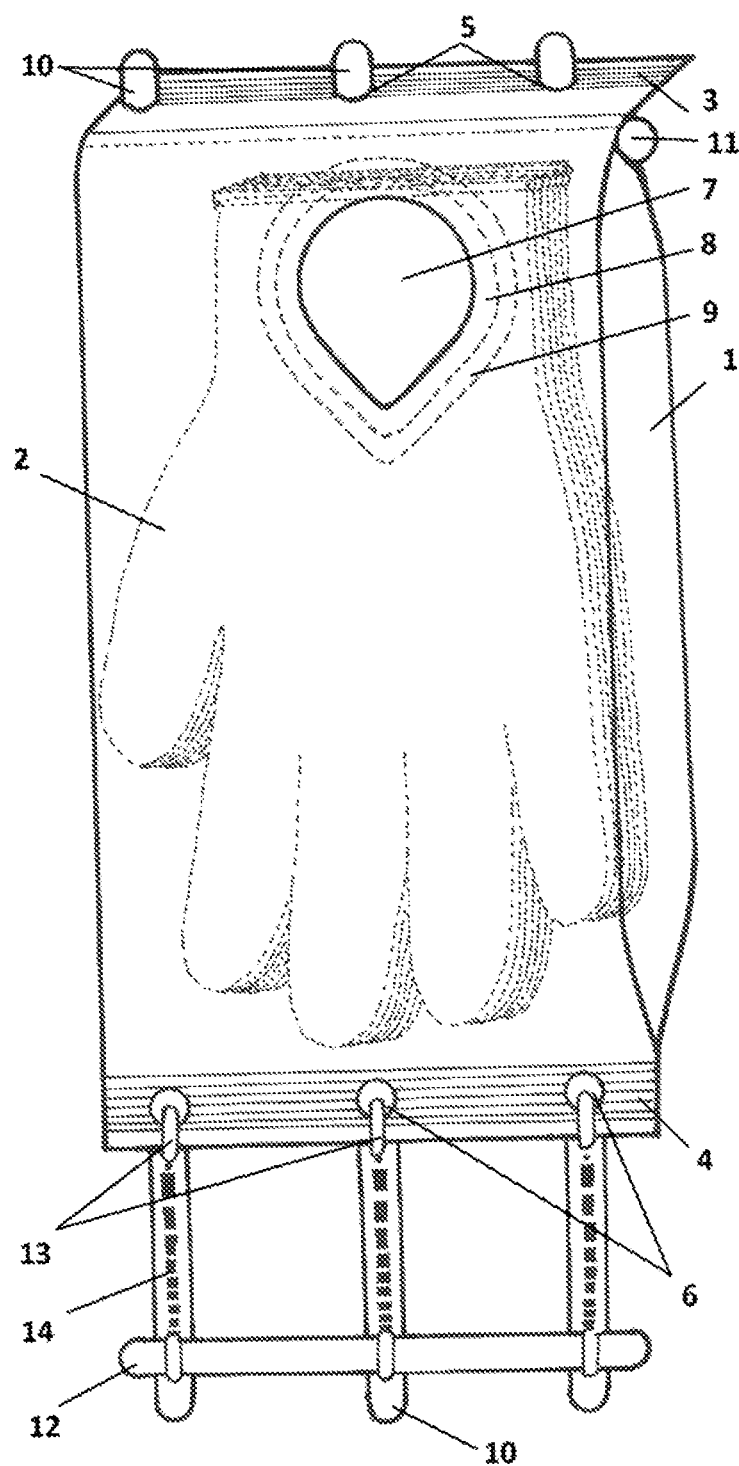
FIG. 1 is a front view of a glove dispensing system.

This disclosure provides and shows that it is possible to develop a solution with less disadvantages of the systems known from the prior art and which can more easily accommodate automated mass production packaging.

This new method of protecting disposable gloves against contamination is special and characterized in that at least one glove is placed in a container (which may be a flexible bag) of a waterproof material, preferably of a plastic, which then closes tightly and where the cuff of at least one glove is positioned near the opening for extracting gloves.

The internal surface of the container may be coated with a biocidal substance.

The container for at least one glove may be attached to a rack which may be tilted at an angle relative to the ground and the opening for extracting gloves may be oriented downwards and towards the ground.

The container for disposable gloves according to this disclosure is special and characterized in that it has an opening for extracting gloves where the opening is protected with a tight closing seal mechanism and at least one glove is placed in the container in such a manner that its cuff is near of the opening used for extracting gloves.

The area of the opening for extracting gloves may be coated with a biocidal substance and the inside of the container may be coated with a biocidal substance.

The glove container may be made of a waterproof material. In various implementations, the material may be plastic.

The container may be in the shape of a bag with seals at the top and bottom portions of the bag. In various implementations, the exterior portion of the seals are perforated to enable attaching the container to the rack.

The dispensing system for disposable gloves according to this disclosure is special and characterized in that it comprises at least one container with at least one glove as well as a rack (which may also be referred to as a dispenser rack) for attaching the container. The container may be in the shape of a bag sealed at the top and bottom and may be attached to the rack where both the top part and the bottom part of the bag are attached to the rack such that the bag is stretched between the fixing points. The container has an opening configured to form a seal with the outermost glove ready to be dispensed from the bag. The cuff of the glove may be in the immediate proximity of the opening.

The container attached to the rack may be tilted in relation to the ground at an angle less than 90 degrees horizontal to the ground. It may be advantageous when this angle is in the range between 30 and 50 degrees.

In various implementations the opening for extracting the glove may be oriented downwards.

The pulling of gloves from the container may not require inserting the hand inside the container and the force of gravity may facilitate extracting the glove and help prevent impurities and water from getting inside the container. In such implementations the risk of contaminating the gloves inside the container is reduced.

In one container there can be one glove or there can be more than one glove. The cuff of each glove is placed in the immediate proximity of the opening for extracting gloves so that the user extracting a glove only grips the cuff and does not touch the other parts of the glove. The opening for extracting gloves is sealable. The closing mechanism can be any closing mechanism known, such as glue-covered film, enabling the hole to be opened and closed multiple times.

The system can comprise more than one container stretched between the racks. The container may be inclined to the horizontal at an angle less than 90 degrees. It is most advantageous when the angle is between 30 and 50 degrees. Such an inclination is optimal as it facilitates the pulling of gloves from the container. In this system, all gloves can be pulled out one at a time in a manner that reduces the risk of the glove being contaminated. The person extracting a glove only touches it with a bare hand at the cuff and after donning it on they can extract another glove and done it on the other hand. Gloves should be packed in such a manner that the cuff of each one of them should be at the height of the opening for extracting them. For gloves that differ from each other depending on whether they are intended for the right or the left hand, they should be packed alternately, or separate containers for right-hand gloves and for left-hand gloves can be used.

The container being made of plastic is designed to enable the coating of its internal surfaces, including the area of the opening, with biocidal substances, which additionally reduces the hazard of the gloves getting contaminated by microbes.

The rack for attaching containers may include hooks on which to hang the containers. For this reason containers should have perforations where the hooks can be placed. It is also possible to use other types of attachments such as clips or clamps. The attachments (including hooks) are connected to the rack by means of a spring or another elastic connector. The rack for containers can be a rigid structure and can also be foldable.

The rack can be mounted on a wall or on a special stand. The rack is attached in such a manner that the container should be at an angle less than 90 degrees relative to the ground.

Implementations of the glove dispenser system disclosed herein may form a solution that enables safer dispensing of disposable gloves in a manner that helps protect them from contamination. In such implementations, the risk of hospital infections, and/or diagnostic errors, resulting from glove contamination may be reduced.

Figure 2:
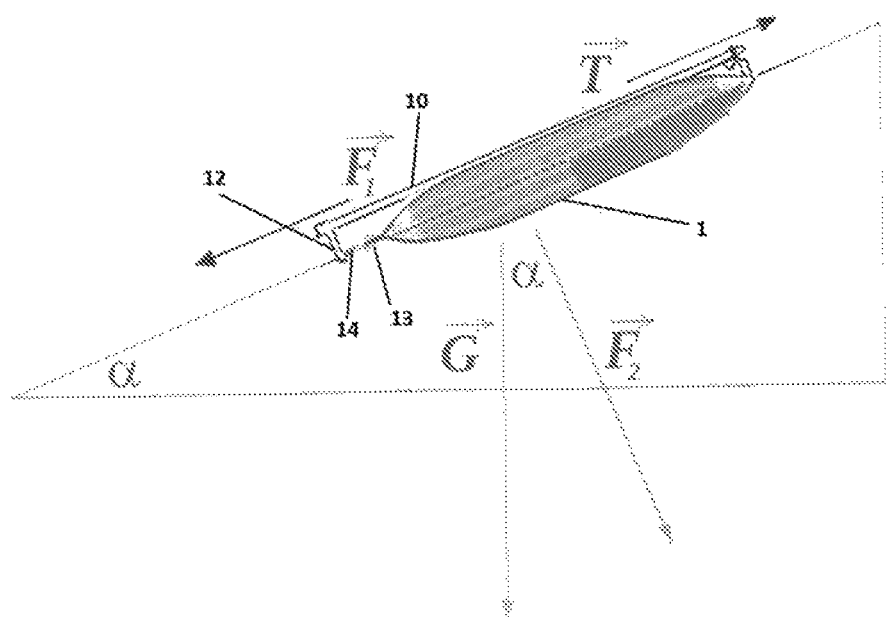
FIG. 2 is a side view of the glove dispensing system of FIG. 1.
Figure 3:
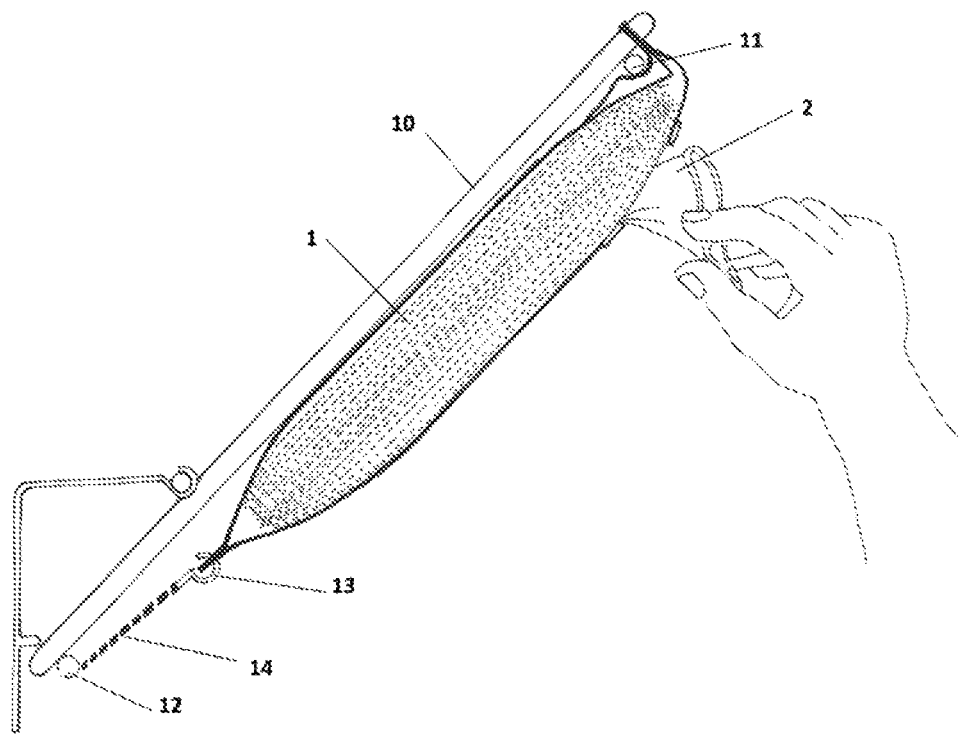
FIG. 3 is a side view of the glove dispensing system of FIG. 1 illustrating how a glove is dispensed.
Figure 4:
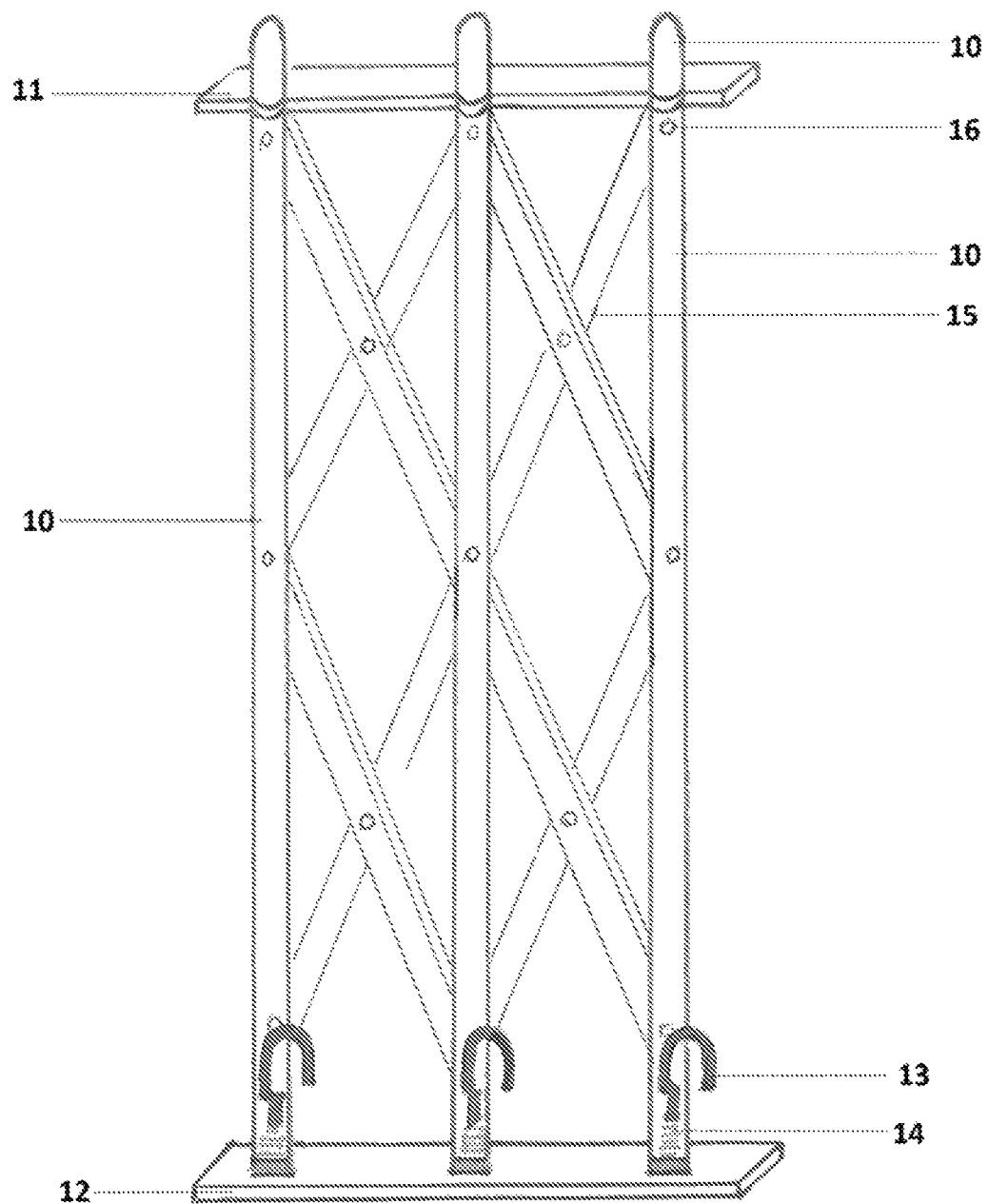
FIG. 4 is a front view of a dispenser rack of the glove dispensing system.

The object of the invention is shown in example drawings where FIG. 1 presents the container for gloves, FIG. 2 presents the container for gloves attached to the rack, FIG. 3 presents the manner of extracting gloves from the container, and FIG. 4 presents a foldable rack for containers.

Example, using FIG. 1 as reference:

The container (1) for disposable gloves (2) is made of a waterproof material which is advantageously of a plastic. Inside the container there are disposable gloves (2). The top part, or first sealed end, of the container (1) is sealed by means of a permanent seal (3) and the bottom part, or second sealed end, of the container (1) is also sealed by means of a permanent seal (4). These permanent seals (3 and 4) may include perforations (5 and 6). In the top part of the container (1) there is an opening (7) for extracting the glove(s) (2). The external surface of the container (1), in the immediate proximity of the opening (7), may be coated with glue (8) where a film (9) covering and securing the opening (7) may be attached. Glue (8) is a type of glue which enables film (9) to be opened and closed multiple times. Vertical pillars (10) of the rack have the container (1) attached in such a manner that the ends of the poles are placed in the perforations (5). Container (1) may rest on the horizontal bracket (11). At the bottom part of the rack there is a horizontal bracket (12) connected to the pillars (10). There are hooks (13) attached to bracket (12) through springs (14). The hooks (13) pass through the perforations (6).

At FIGS. 2 and 3, please see that the container (1) is attached to pillars (10) which are tilted at an angle (a) relative to the ground. In various implementations, the top part of the container (1) may be attached to the pillars (10) and the bottom part (of the container) may be attached to the bracket (12) by means of a system of hooks (13) with springs or elastic (14). The force of gravity (G) helps a glove to move freely downwards. The container is stretched on the rack and it is acted on by a force of tension (T). When a glove (2 FIG. 3) is pulled out of the container the container is additionally acted on by a force (F2 FIG. 2) and at the same time a force (F1) generated by the springs (14).

At FIG. 4 please see that the rack for attaching containers consists of vertical poles (10) and horizontal brackets (11 and 12). The bottom horizontal bracket (12) has hooks (13) attached to it on springs or elastic (14). The rack is reinforced with diagonal brackets (15) which are connected to the poles (10) by means of hardware connectors (16).

Figure 9:
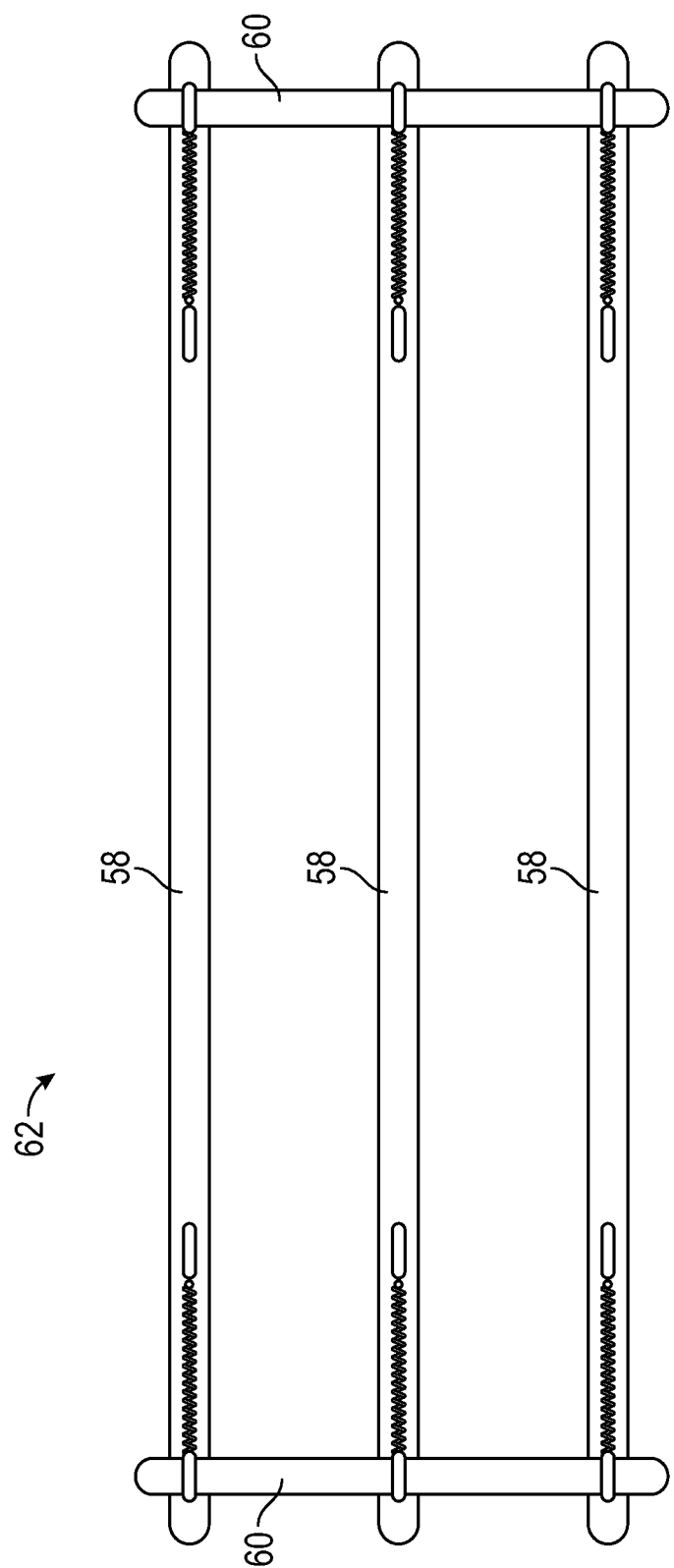
FIG. 9 is a front view of a non-collapsible dispenser rack.

While the dispenser rack of FIG. 4 is illustrated as foldable or collapsible, in other implementations the dispenser rack may not be collapsible. Referring to FIG. 9, a front view of a non-collapsible dispenser rack is illustrated. In various implementations, the dispenser rack 62 may include two or more pillars 58 coupled between two brackets 60. In various implementations, the dispenser rack 62 may include a plurality of springs 64 coupled to each of the brackets. In other implementations, the dispenser rack may include a plurality of springs coupled to only one of the two brackets. In various implementations, and as illustrated by FIG. 9, the plurality of springs may include a spring positioned over each end of each pillar of the two or more pillars 58. In other implementations, the plurality of springs may include more or less springs than what is illustrated by FIG. 9.

Figure 5:
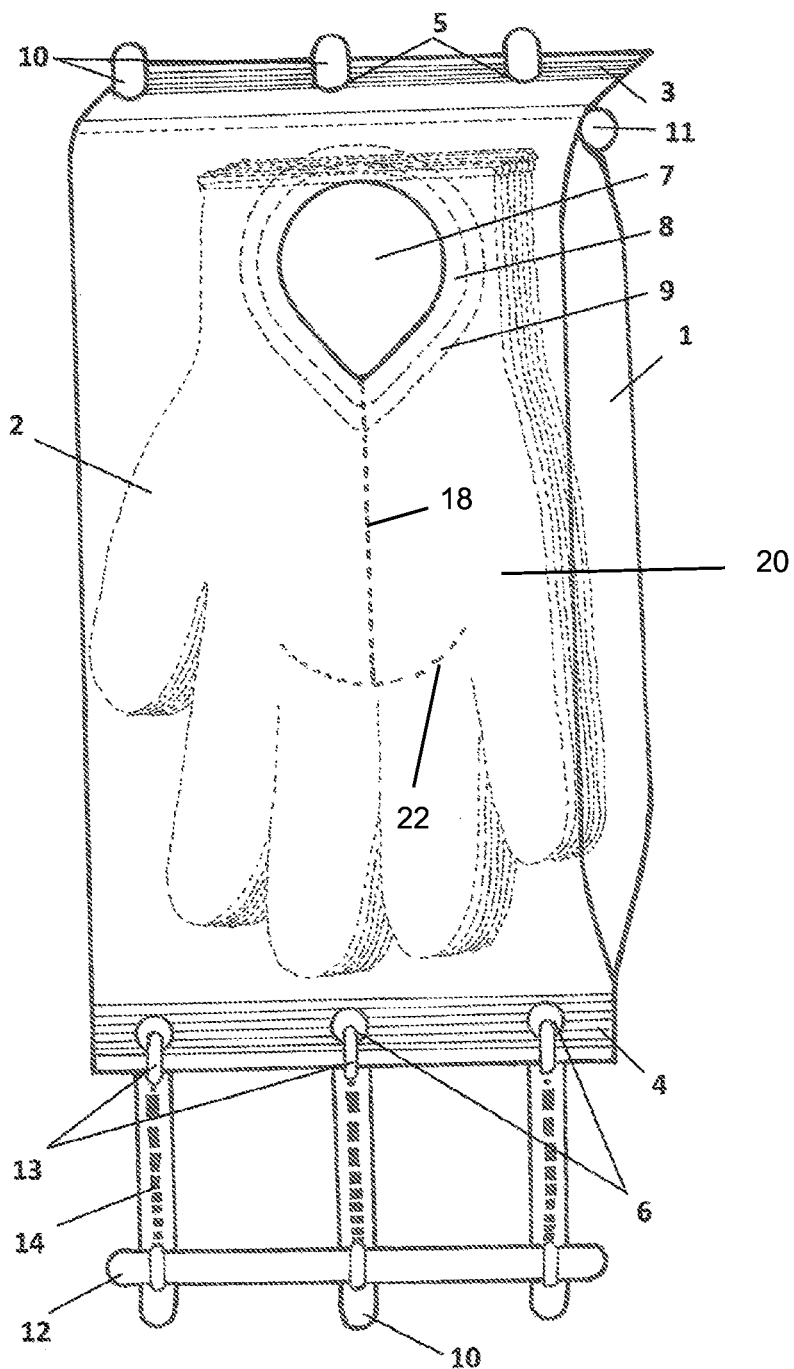
FIG. 5 is a front view of the glove dispensing system of FIG. 1 having a first implementation of a perforated slit.
Figure 6:
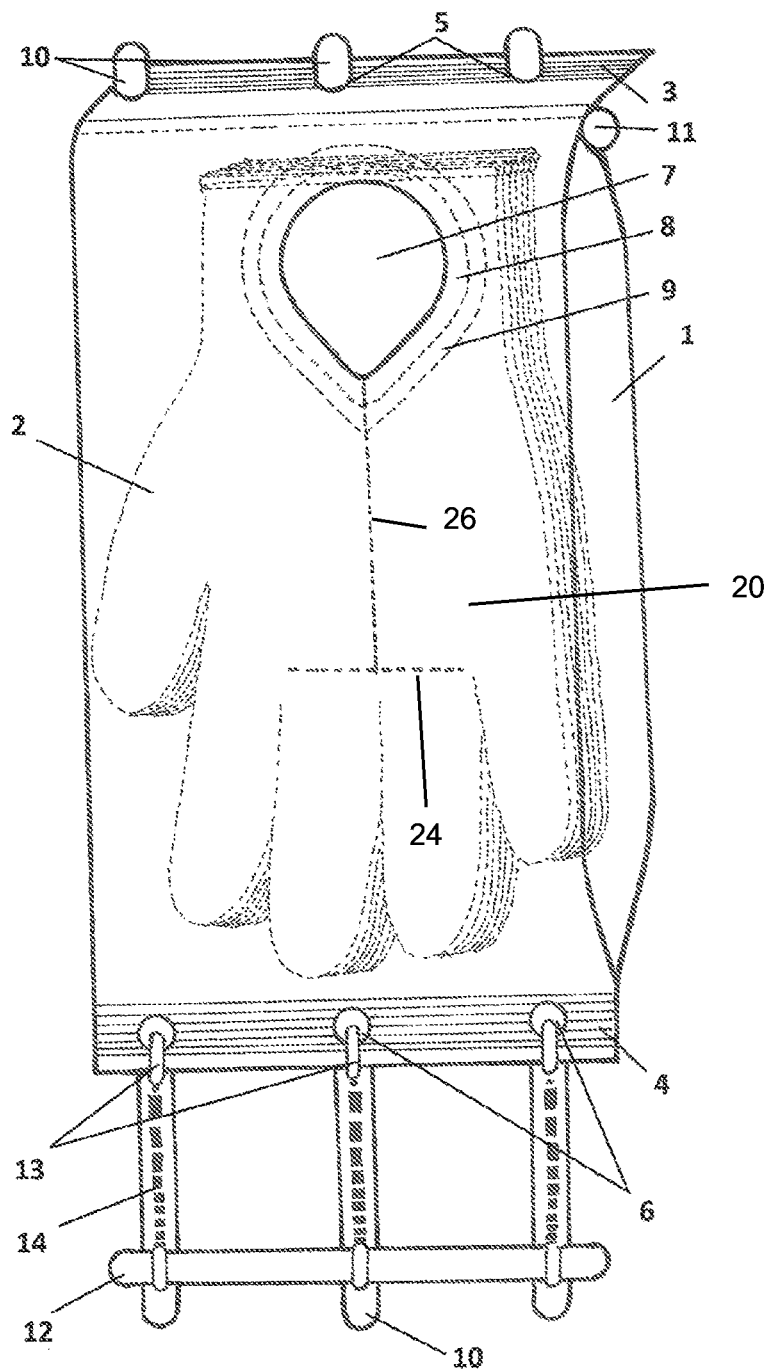
FIG. 6 is a front view of the glove dispensing system of FIG. 1 having a second implementation of a perforated slit.

Referring to FIG. 5, a front view of the glove dispensing system of FIG. 1 having a first implementation of a perforated slit is illustrated. In various supplementations, the sidewall including the opening 7 of the container 1, or flexible bag, may also include a perforated slit 18 extending from the opening 7. As illustrated, the perforated slit 18 may extend parallel to the longest length of the container 1. In various implementations, and as illustrated by FIG. 5, sidewall 20 may include a second perforated slit 22 formed adjacent to an end of the perforated slit 18. In such implementations, the second perforated slit 22 may be substantially perpendicular to the first perforated slit 18. While FIG. 5 illustrates the second perforated slit 22 as curved with the concave portion of the slit facing the opening 7, in other implementations the concave portion of the perforated slit 22 may face away from the opening 7. In other implementations, as illustrated by FIG. 6, the sidewall 20 may include a second slit 24 perpendicular to a first slit 26 which is straight. In still other implementations, other designs and/or number of slits may be included in the sidewall 20 of the bag. While the implementations of the slits disclosed herein are perforated, in other implementations the slits may not be perforated but may be continuously open. In other implementations, the slits may be configured to facilitate the dispensing of a glove from the bag.

Figure 7:
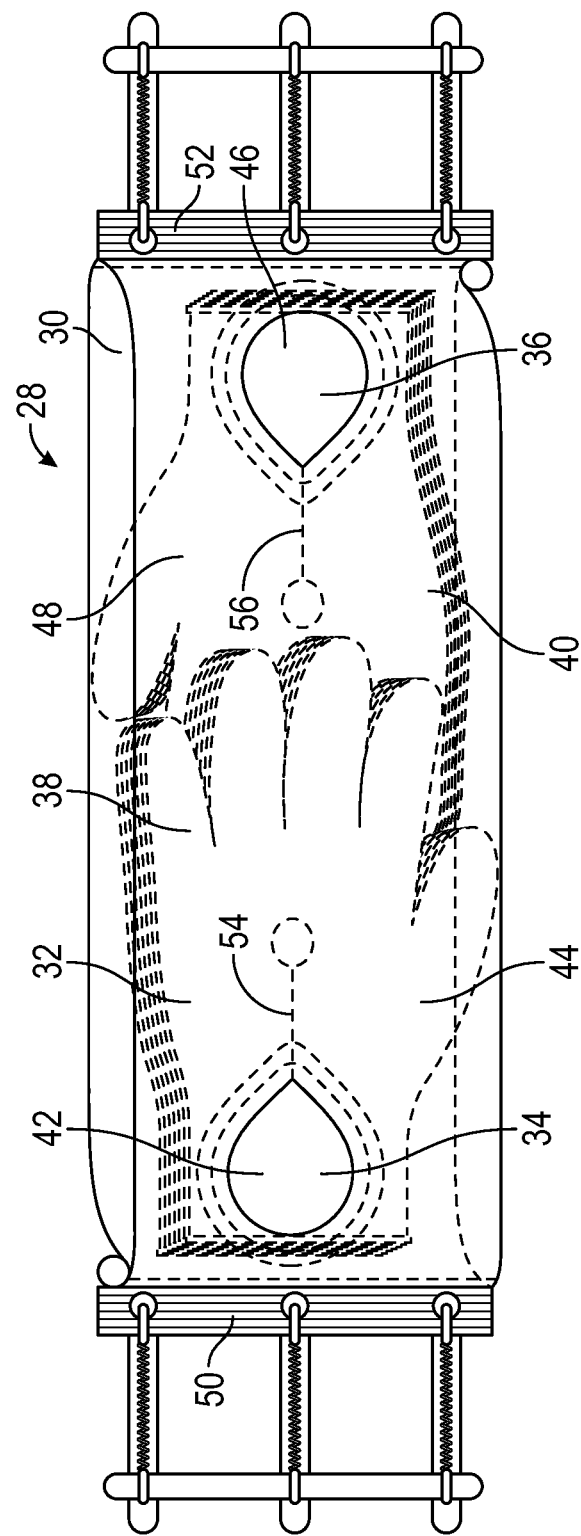
FIG. 7 is a front view of a glove dispensing system configured to dispense multiple gloves at the same time.
Figure 8:
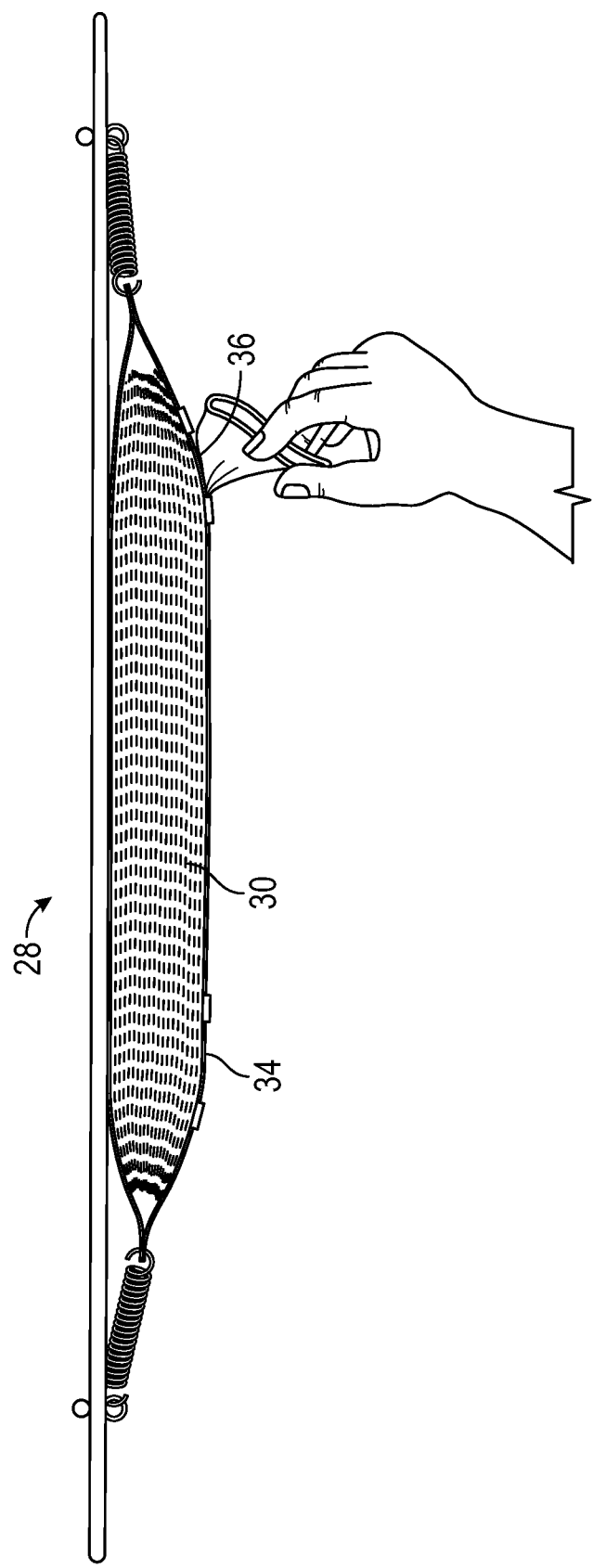
FIG. 8 is a side view of the glove dispensing system of FIG. 7 having a glove dispensed.

Referring to FIG. 7, a front view of a glove dispensing system configured to dispense multiple gloves at the same time is illustrated, and referring to FIG. 8, a side view of the glove dispensing system of FIG. 7 having a glove dispensed is illustrated. The glove dispensing system 28 of FIG. 7 may include any other elements of any other glove dispensing system disclosed herein. In various implementations, the glove dispensing system 28 is configured to dispense two gloves at the same time. In such implementations, the glove dispensing system 28 may include a flexible bag 30 having a sidewall 32. The sidewall 32 includes a first opening 34 and a second opening 36. The flexible bag 30 also includes a first plurality of gloves 38 and a second plurality of gloves 40. A cuff 42 of the outermost glove 44 of the first plurality of gloves 38 may be accessible through the opening 34. Similarly, a cuff 46 of the outermost glove 48 of the second plurality of gloves 40 may also be accessible through the second opening 36. In various implementations, a seal may be formed between the outermost glove 44 and the inner surface of the sidewall 32. A seal may also be formed between the outermost glove 48 and the inner surface of the sidewall 32. In such implementations, contaminants may be incapable of accessing the interior of the flexible bag 30 due to the seals formed. In various implementations, the seals may be formed through a tension applied to the flexible bag which stretches flexible bag 30 between the first and 50 and the second and 52 of the bag 30, and in turn, presses the outer most glove against an inner sidewall of the flexible bag.

In various implementations the first plurality of gloves 32 may include right-handed gloves and the second plurality of gloves 40 may include left-handed gloves. In other implementations, the first plurality of gloves 32 may include left-handed gloves and the second plurality of gloves 40 may include right-handed gloves. In still other implementations, either of or both the first plurality of gloves 32 and the second plurality of gloves 40 may fit either a right or left hand.

In various implementations, the fingers of the first plurality of gloves 32 may overlap the figures of the second plurality of gloves 40. In other implementations, the fingers of the first plurality of gloves may not overlap the fingers of the second plurality of gloves. As illustrated, the fingers of the first plurality of gloves may extend towards the second opening 36 and the fingers of the second plurality of gloves may extend towards the first opening 34. In other implementations, the glove may be arranged differently than what is illustrated by FIG. 7.

In various implementations, the sidewall 30 may include a first perforated slit 54 extending from the first opening 34 and/or a second perforated slit 56 extending from the second opening 36. In other implementations, the sidewall 30 may include any other type of slit disclosed herein. In still other implementations, the sidewall 30 may not include a first perforated slit 54 and/or a second perforated slit 56.

Any of the implementations disclosed herein may include an opening to access the gloves that is reclosable. In such implementations, the bag may include a cover for the opening. In other implementations, any of the implementations disclosed herein may not include a cover for the opening to access the gloves.

In any of the implementations disclosed herein, the bag of the glove dispensing system may be configured to have a tension applied between the first end and the second end of the bag. This tension may be applied from a dispenser rack. The dispenser rack may be configured to couple directly to a first plurality of openings in a first end of the bag and/or a second plurality of openings in a second end of the bag. In other implementations, the first end of the bag may not include a first plurality of openings and the second of the bag may not include a second plurality of openings. In such implementations, the dispenser rack may be configured to couple to the first end of the bag and the second end of the bag through a clip, clasp, tie, or any other coupling mechanism. Due to this tension, pressure is applied between the inner sidewalls of the bag and the plurality of gloves stored within the bag. The pressure applied may result in a seal being formed between the outermost glove and an inner sidewall of the bag. This pressure may result in a seal preventing contaminants from entering the bag. The tension applied to the bag may result from, by non-limiting example, one or more springs, elastic properties of the bag, other elastic mechanisms coupled to the bag, manual tension applied to the bag by a user, or any other mechanism configured to apply tension between the first and the second end of the bag. This tension may also facilitate the retention of the gloves in a particular position and/or orientation within the bag and may help the cuffs of the plurality of gloves in bag made accessible through the opening in the sidewall of the bag.

While this disclosure discloses various dispenser racks configured to apply tension to the flexible bag and couple to the flexible bag, it is understood that a flexible bag may be coupled to a dispenser racks in a manner that results in the flexible bag being horizontal, vertical, or at any other angle in relation to a floor and/or ground. In particular implementations, the dispenser rack may include magnets (which magnets may be coupled to a wall). In such implementations, the flexible bag may have corresponding magnets or metallic elements configured to couple to the magnets on the wall. In still other implementations, the bag may include magnetic elements configured to couple to metallic elements fixed to a wall.

In various implementations, the dispenser rack may include hooks or other coupling mechanisms directly configured to directly couple to a wall or other surface. In such implementations, the dispenser rack may be configured to be used on a wall, in an ambulance, or any other place configured to have a plurality of hooks or other coupling mechanisms coupled thereto.

In still other implementations, any of the containers or flexible bags disclosed herein may be configured to dispense bags without a dispenser rack. In such implementations, the bag may be freestanding and a user may access the gloves through the bag without the tension applied between the first sealed end and the second sealed end of the bag. In particular implementations, the bag may be laid flat and the force of gravity may facilitate the formation of a seal between the outermost glove and the sidewall of the bag as the sidewall of the bag rests upon the outermost glove within the bag.

Any implementations of the flexible bags or containers disclosed herein may be configured to accommodate vacuum packaging of the plurality of gloves within the bag. In such implementations, the bags may be more compact and may save space during shipping and storage of the flexible bags.

In places where the description above refers to particular implementations of glove dispensing systems and implementing components, sub-components, methods and sub-methods, it should be readily apparent that a number of modifications may be made without departing from the spirit thereof and that these implementations, implementing components, sub-components, methods and sub-methods may be applied to other glove dispensing systems.

What is claimed is:

1. A glove dispenser comprising:
   a flexible bag comprising:
      a sealed first end and a sealed second end opposite the sealed first end;
      a first plurality of openings extending through the sealed first end;
      a second plurality of openings extending through the sealed second end; and
      a first opening extending through a sidewall of the flexible bag; and
   a first plurality of gloves comprised within the flexible bag, wherein a cuff of a glove of the first plurality of gloves is exposed through the first opening;
   wherein the first plurality of openings and the second plurality of openings are configured to couple to a dispenser rack; and
   wherein the glove dispenser is configured to stretch between the sealed first end and the sealed second end when coupled to the dispenser rack.

2. The glove dispenser of claim 1, further comprising a perforated slit formed in the sidewall of the flexible bag and extending from the first opening.

3. The glove dispenser of claim 1, wherein an interior of the flexible bag is coated with a biocide.

4. The glove dispenser of claim 1, further comprising a second opening extending through the sidewall of the flexible bag.

5. The glove dispenser of claim 4, further comprising a second plurality of gloves comprised within the flexible bag, wherein a cuff of a glove of the second plurality of gloves is accessible through the second opening.

6. A glove dispensing system comprising:
   a flexible bag comprising:
      a sealed first end and a sealed second end, the sealed first end opposite the sealed second end; and
      an opening extending through a sidewall of the flexible bag;
   a plurality of gloves comprised within the flexible bag, wherein a cuff of a glove of the plurality of gloves is accessible through the opening; and
   a dispenser rack coupled to the flexible bag;
   wherein the dispenser rack is configured to apply tension to the flexible bag between the sealed first end and the sealed second end; and
   wherein the dispenser rack stretches the flexible bag and compresses the plurality of gloves between two inner sidewalls of the flexible bag.

7. The glove dispensing system of claim 6, wherein the dispenser rack comprises a plurality of springs configured to stretch the flexible bag between the sealed first end and the sealed second end.

8. The glove dispensing system of claim 7, wherein the plurality of springs are coupled to the sealed first end.

9. The glove dispensing system of claim 7, wherein the plurality of springs are coupled to the sealed second end.

10. The glove dispenser system of claim 6, wherein the opening is closable.

11. A glove dispensing system comprising:
    a flexible bag comprising:
       a sealed first end and a sealed second end;
       a first opening extending through a sidewall of the flexible bag; and
       a second opening extending through the sidewall of the flexible bag;
    a first plurality of gloves comprised within the flexible bag, wherein a cuff of a glove of the first plurality of gloves is accessible through the first opening;
    a second plurality of gloves comprised within the flexible bag, wherein a cuff of a glove of the second plurality of gloves is accessible through the second opening; and
    a dispenser rack coupled to the flexible bag;
    wherein the dispenser rack is configured to apply tension to the flexible bag between the sealed first end and the sealed second end; and
    wherein the dispenser rack stretches the flexible bag and compresses the first plurality of gloves between two inner sidewalls of the flexible bag, thereby forming a first seal between a first inner sidewall of the two inner sidewalls of the flexible bag and the glove accessible through the first opening.

12. The glove dispenser system of claim 11, wherein an interior of the flexible bag is coated with a biocide.

13. The glove dispensing system of claim 11, wherein the dispenser rack comprises a plurality of springs configured to stretch the flexible bag between the sealed first end and the sealed second end.

14. The glove dispensing system of claim 13, wherein the plurality of springs are coupled to a plurality of openings comprised in the first sealed end.

15. The glove dispensing system of claim 13, wherein the plurality of springs are coupled to a plurality of openings comprised in the second sealed and.

16. The glove dispenser system of claim 11, wherein the dispenser rack stretches the flexible bag and compresses the second plurality of gloves between two inner sidewalls of the flexible bag, thereby forming a second seal between the first inner sidewall of the two inner sidewalls of the flexible bag and the glove accessible through the second opening.

17. The glove dispenser system of claim 11, wherein the first opening is closable and the second opening is closable.

18. The glove dispenser system of claim 11, wherein the first plurality of gloves comprise right-handed gloves and the second plurality of gloves comprise left-handed gloves.

* * * * *